United States Patent
Saunders et al.

(10) Patent No.: US 6,739,138 B2
(45) Date of Patent: May 25, 2004

(54) THERMOELECTRIC MODULES AND A HEATING AND COOLING APPARATUS INCORPORATING SAME

(75) Inventors: John Saunders, Naperville, IL (US); Jamey D. Jacob, Lexington, KY (US); Dayong Gao, Lexington, KY (US); Michel A. Myers, Darien, IL (US)

(73) Assignee: Innovations Inc., Alexandria, VA (US)

( * ) Notice: Subject to any disclaimer, the term of this patent is extended or adjusted under 35 U.S.C. 154(b) by 82 days.

(21) Appl. No.: 10/186,618

(22) Filed: Jul. 2, 2002

(65) Prior Publication Data

US 2003/0097845 A1 May 29, 2003

Related U.S. Application Data

(60) Provisional application No. 60/332,545, filed on Nov. 26, 2001.

(51) Int. Cl.$^7$ .................................. F25B 21/02
(52) U.S. Cl. .................. 62/3.3; 62/3.2; 62/3.6; 62/3.7
(58) Field of Search ................ 62/3.3, 3.2, 3.6, 62/3.7

(56) References Cited

U.S. PATENT DOCUMENTS

| | | | |
|---|---|---|---|
| 5,800,490 A | | 9/1998 | Patz et al. |
| 5,970,718 A | | 10/1999 | Arnold |
| 6,384,312 B1 | * | 5/2002 | Ghoshal et al. ............ 136/203 |
| 6,392,486 B1 | * | 5/2002 | Lemay, Jr. ................. 330/253 |
| 6,402,739 B1 | * | 6/2002 | Neev ............................ 606/9 |
| 2002/0019725 A1 | * | 2/2002 | Petite ........................ 702/188 |
| 2002/0026226 A1 | * | 2/2002 | Ein ............................ 607/108 |
| 2002/0047775 A1 | * | 4/2002 | del Castillo et al. ....... 340/3.54 |
| 2002/0143966 A1 | * | 10/2002 | Sibecas et al. ............. 709/229 |
| 2002/0145538 A1 | * | 10/2002 | Bocko et al. .......... 340/870.28 |
| 2002/0178789 A1 | | 12/2002 | Sunshine et al. |

OTHER PUBLICATIONS

Peltier; Sep. 18, 2001; pp. 1–15; www.naijiw.com/peltier/peltier.html.
Peltier Device Information Directory; pp. 1–5; www.peltier–info,com/info.html.
Peltier Device Information Directory; pp. 1–4; www.peltier–info.com/photos.html.
Peltier Coolers; Novel Concepts, Inc.; p. 1–4; www.novel-conceptsinc.com/peltier.htm.

* cited by examiner

*Primary Examiner*—Timothy L. Maust
*Assistant Examiner*—Mark Shulman
(74) *Attorney, Agent, or Firm*—Antonelli, Terry, Stout, & Kraus, LLP

(57) ABSTRACT

A heating and cooling apparatus to be applied to an object to control the temperature of the object. A number of thermoelectric modules are adapted to be positioned in contact with the object in a pattern. A voltage source is adapted to apply a voltage to the thermoelectric modules to cause a temperature change in each thermoelectric module so as to control the temperature of the object in accordance with the pattern and with the voltage applied to thermoelectric modules.

53 Claims, 9 Drawing Sheets

THERMOELECTRIC MODULES AND A HEATING AND COOLING APPARATUS INCORPORATING SAME

CROSS-REFERENCE TO RELATED APPLICATION

This application claims the benefit of provisional application Serial No. 60/332,545 filed Nov. 26, 2001.

FIELD OF THE INVENTION

The present invention pertains to thermoelectric modules and to a heating and cooling apparatus for controlling the temperature of an object, either an inanimate object or an animate object, such as a human body. By way of example, with reference to application of the heating and cooling apparatus to an object such as a human body, the apparatus might be used to treat injuries or might be incorporated into clothing, including being used as a thermal control garment in protective clothing. Likewise, the apparatus might be used for signature profile modification or to provide thermal masking to camouflage personal, material, or equipment.

BACKGROUND OF THE INVENTION

There are frequent needs for portable heating or cooling devices. By way of example, muscle and tissue injuries might be treated by heating, cooling, massaging, and electrically stimulating the injured area. A heating or cooling apparatus might be incorporated into a protective wrap to be positioned around the injured body part to heat or cool the injured body part, as desired. Likewise, a heating or cooling apparatus might be incorporated into protective clothing to enable a person to enter an area of extreme temperature, for example a fire fighter going into a building that is on fire. A person who has suffered from extensive burns to the body must be kept warm, for example beneath a blanket or other covering which provides heat. Another application of a portable heating and cooling apparatus is a portable cooler, for example for holding temperature-sensitive material, such as blood during transportation, or such as a picnic cooler. Further, temperature variations can be utilized to provide signature profile modification, thermal masking, or camouflage. While thermoelectric modules such as Peltier devices can be conveniently incorporated into various types of heating and cooling apparatus, known thermoelectric modules permit undesirable heat transfer from their heat releasing substrate panel, through the module interior, to their heat absorbing substrate panel. This significantly reduces the efficiency of the thermoelectric module.

In the past, injuries requiring cold compresses have often been treated by a cloth or bandage that has been cooled in a freezer and applied to the injured area. Ice packs have also been used to apply cooling therapy to a body surface. Injuries requiring heat treatment have often treated by a cloth or bandage that has been heated in, for example, a microwave oven, and then applied to the injured area. Similarly, heating pads and chemical salts have been applied to an injured area that requires heat therapy U.S. Pat. No. 5,800,490, the disclosure of which is incorporated herein by reference, discusses various heating and cooling devices that have been used in the past for therapeutic purposes.

These different apparatuses have various shortcomings. Ice packs and heated cloths, for example, return to ambient temperature in a relatively short time. Other apparatuses likewise have drawbacks, such as requiring a non-portable energy source or such as being capable of inadvertent or improper operation if not being worn properly.

SUMMARY OF THE INVENTION

The present invention is a heating and cooling apparatus adapted to be applied to an object to control the temperature of the object, whether the object be an inanimate object or an animate object such as a person. A heating and cooling apparatus in accordance with a preferred embodiment of the invention includes a plurality of thermoelectric modules adapted to contact the object in a pattern, and a power source enabling each thermoelectric module to create a temperature difference module so as to control the temperature of the object in accordance with the pattern.

Each thermoelectric module includes a plurality of semiconductor pellets positioned between first and second thermal conduction layers or substrate panels. The plurality of thermoelectric modules can be positioned with their substrate panels defining substantially continuous surfaces. Alternatively, the plurality of thermoelectric modules can be positioned such that a substantially continuous surface is defined by the first substrate panels of some of the thermoelectric modules and the second substrate panels of others of the thermoelectric modules. If desired, a twisted portion can join the two portions of the continuous surface.

The heating and cooling apparatus can further include an electrical stimulating device to apply an electrical stimulus to the body and/or a pressure device to apply pressure to the body. Further, temperature sensors can be incorporated to permit monitoring of the temperature of the various thermoelectric modules as well as pressure sensors to monitor applied pressure.

The power source can include a voltage supply for supplying the voltage and a controller for controlling and/or monitoring the supplied voltage and associated current. The controller might be a read only memory or a field programmable gate array. Alternatively the controller might comprise a processor and a memory for storing a program for the processor, or a set of processors and associated memories. Alternatively, the voltage source further can include one or more input units connected to the controller to receive input signals and to apply the received input signals to the controller to determine the control of the supplied voltage. The input unit call be a keypad on the heating and cooling apparatus or a wireless receiver, such as a Bluetooth receiver. Likewise, the input unit can include a jack connection permitting a signal source to be connected by a wire connector. Further the controller can include an authentication unit for receiving an authentication code authenticating the received input signals as being from an authorized source.

The controller might provide a uniform voltage signal or a variable voltage signal, and might provide different voltage signals to different ones of the thermoelectric modules.

In another aspect, the present invention is a thermoelectric module made up of a number of semiconductor pellets joined in a series circuit to a voltage source. The semiconductor pellets are positioned between first and second thermal conduction layers. A thermal barrier inhibits heat transfer through the module interior from the heat releasing thermal conduction layer to the heat absorbing thermal conduction layer. The thermal barrier might be provided by a vacuum within the module interior around the semiconductor pellets. Alternatively, the thermal barrier might be provided by a suitable insulating material within the module interior, around the pellets.

In a further aspect, the present invention is a heating and cooling apparatus including first and second thermoelectric modules. A voltage source is connected across the first thermoelectric module, causing temperature changes in the thermal conduction layers of that module. A thermal conductor connects the heated thermal conduction layer panel of the first thermoelectric module with a corresponding thermal conduction layer of the second thermoelectric module so as to heat that layer and create a temperature difference across the second thermoelectric module. This results in a voltage difference across the second thermoelectric module. A voltage sensor is connected across the second thermocectrical module to measure that voltage.

BRIEF DESCRIPTION OF THE DRAWINGS

These and other aspects and advantages of the present invention are more apparent from the following detailed description and claims, particularly when considered in conjunction with the accompanying drawings. In the drawings:

Figure 3A:
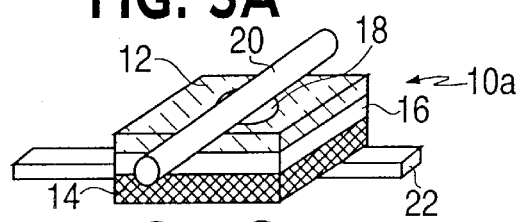
Figure 3B:
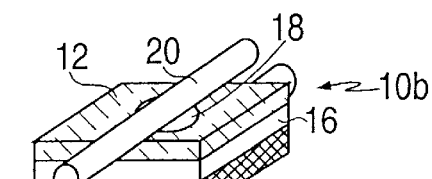
Figure 3C:
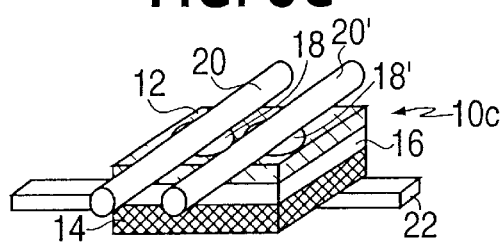
Figure 5:
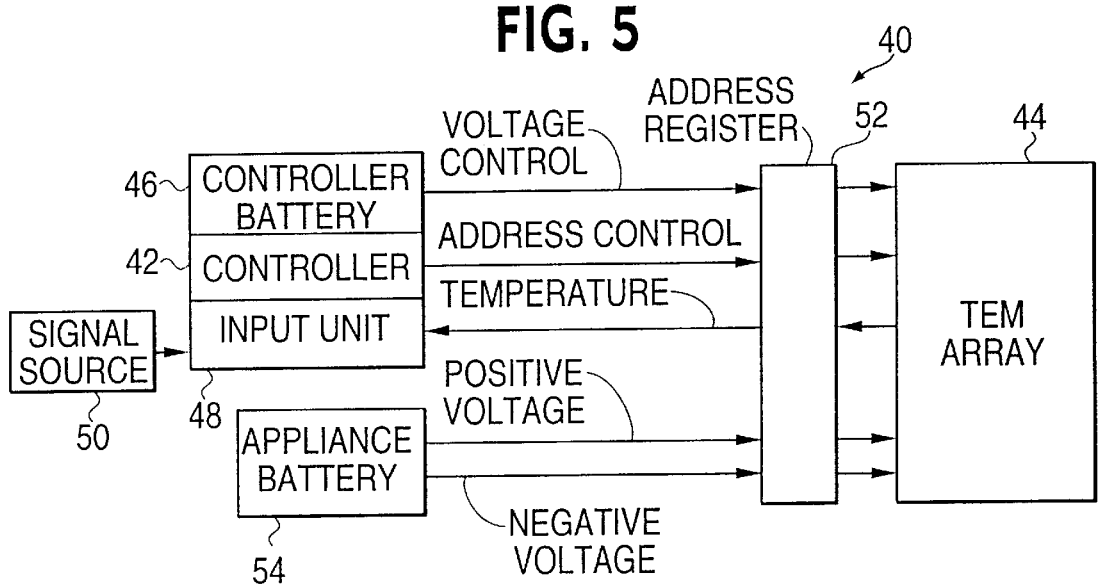
Figure 6A:
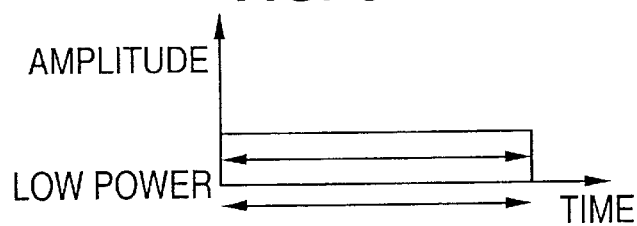
Figure 6B:
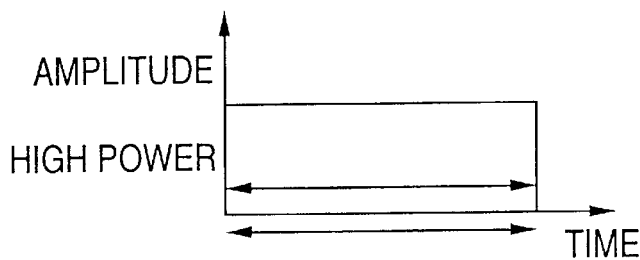
Figure 6B:
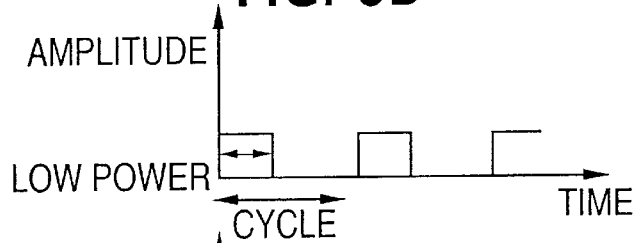
Figure 6C:
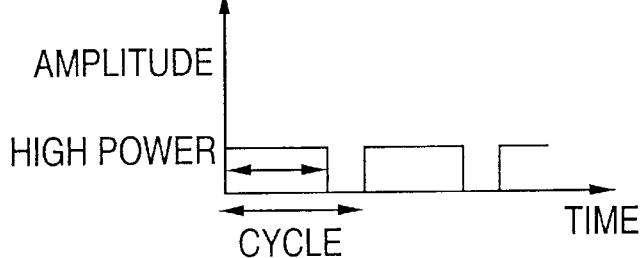
Figure 6C:
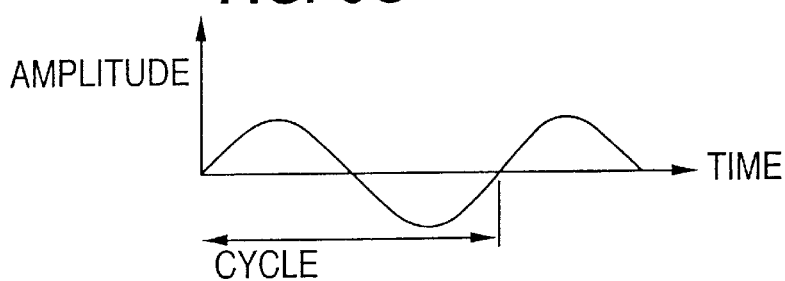

Each of FIGS. 3A, 3B, and 3C is a schematic representation of an embodiment of a thermoelectric module in accordance with the present invention;

Each of FIGS. 4A–4G depicts a pattern of thermoelectric modules which might be incorporated into a heating and cooling apparatus in accordance with an embodiment of the present invention;

FIG. 5 is a block diagram of an embodiment of a heating and cooling apparatus in accordance with the present invention;

FIG. 6A is a timing diagram illustrating the application of voltages of different levels to a heating and cooling apparatus in accordance with an embodiment of the present invention;

FIG. 6B is a timing diagram illustrating the application of voltage pulses of different levels to a heating and cooling apparatus in accordance with another embodiment of the present invention;

FIG. 6C is a timing diagram depicting the application of a voltage which periodically varies in direction to a heating and cooling apparatus in accordance with an embodiment of the present invention.

Figure 7:
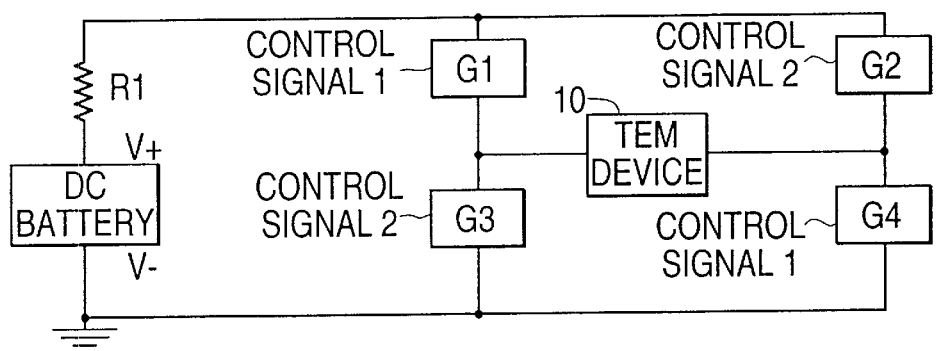

FIG. 7 is a schematic representation of a thermoelectric array control technique in accordance with an embodiment of the present invention.

Figure 11:
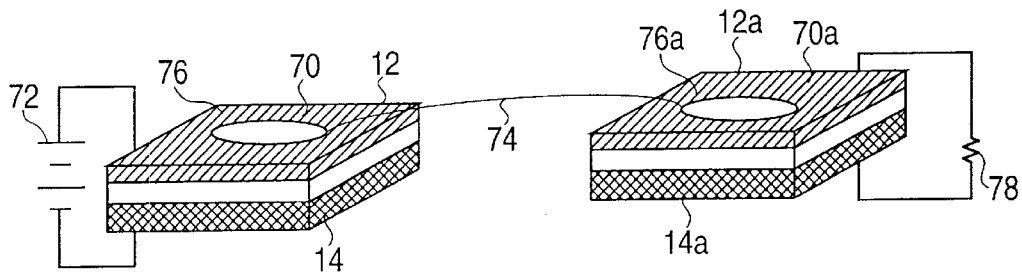
Figure 9:
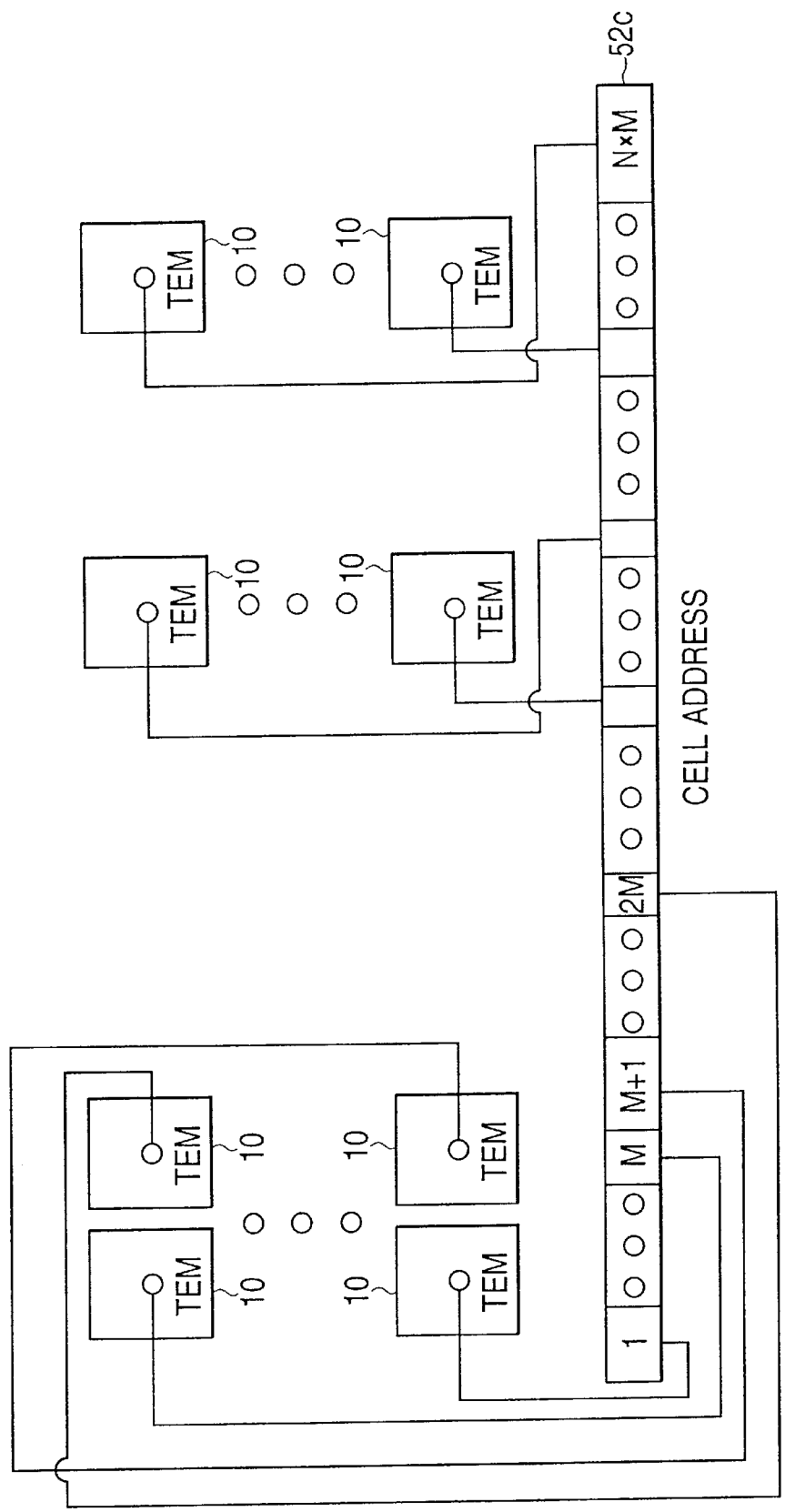

Each of FIGS. 8A–8D is a diagram illustrating dynamic switching of modules within an array to different energization states of the thermoelectric modules in a heating and cooling apparatus in accordance with an embodiment of the present invention;

FIG. 9 is a schematic diagram illustrating another scheme for addressing thermoelectric modules in a heating and cooling apparatus in accordance with the present invention;

Each of FIGS. 10A–10D is a diagram illustrating different energization states of a thermoelectric module in a heating and cooling apparatus in accordance with another embodiment of the present invention; and FIG. 11 is a schematic representation illustrating a heating and cooling apparatus in accordance with another embodiment of the present invention.

DETAILED DESCRIPTION

Figure 1:
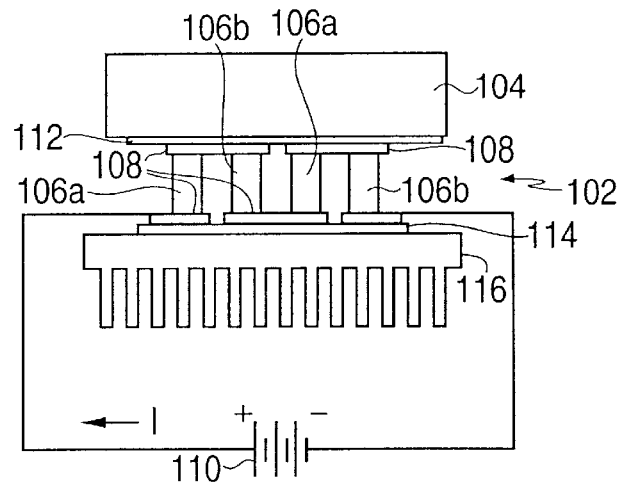
FIG. 1 is a schematic representation of a conventional thermoelectric module and its associated hardware used to dissipate the generated heat.

FIG. 1 is a schematic representation of a conventional thermoelectric module or Peltier module 102 connected to cool an object 104. Thermoelectric module 102 includes a plurality of semiconductor pellets 106. The adjacent pellets 106 are of opposite semiconductor type; that is, every other pellet 106a is P-type semiconductor material, while the intervening pellets 106b are N-type semiconductor material. Adjacent pellets are connected by electrically conductive members 108, for example of copper, to form a series circuit, the ends of which are connected to the terminals of a DC voltage source 110. The upper conductive strips as depicted in FIG. 1 contact one surface of a first thermally conductive, electrically insulating substrate panel 112, the opposite surface of which contacts the object 104 to be cooled. In like manner, the lower conductive strips as depicted in FIG. 1 contact one surface of a second thermally conductive electrically insulating substrate panel 114 the opposite surface of which contacts a heat sink 116. If desired, means such as a fan can be utilized to remove heat from heat sink 116. Substrate panels 112 and 114, pellets 106, and electrically conductive members 108 thus form thermoelectric module 102

When current from voltage source 110 flows from one of the conductive strips 108 into a P-type pellet 106a or from an N-type pellet 106b into one of the conductive strips 108, heat is given off into the surroundings. When current from voltage source 110 flows from one of the P-type pellets 106a into one of the conductive strips 108 or from one of the conductive strips 108 into an N-type pellet 106b, heat is absorbed from the surroundings. Thus, when connected as depicted in FIG. 1, thermoelectric module 102 absorbs heat from its surroundings through first substrate panel 112 and releases heat to its surroundings through second substrate panel 114. Since first substrate panel 112 is contacting object 104, semiconductor pellets 106 absorb heat from the object and so cool the object. Likewise, since second substrate panel 114 is contacting heat sink 116, semiconductor pellets 106 transfer heat to the heat sink. In FIG. 1 the current is shown as flowing in a clockwise path from the positive terminal of voltage source 110, through thermoelectric module 102, and to the negative terminal of voltage source 110. If voltage source 110 is reversed so as to cause current to flow in a counterclockwise path, heat would be absorbed through second substrate panel 114 and released through first substrate panel 112.

More information about Peltier devices is available in literature and from the Internet, for example at www.naijiw.com/peltier/peltier.html and at www.peltier-info.com/info.html.

The thermoelectric module itself also produces heat due to the voltage across it and the current through it. Further, as second substrate panel 114 absorbs heat, a portion of that heat is transferred by radiation or convection through the interior of thermoelectric module 102 to first substrate panel 112 This heat transfer back to the cool side of thermoelectric module 102 reduces the efficiency of the thermoelectric module and wastes power from voltage source 110.

Figure 2A:
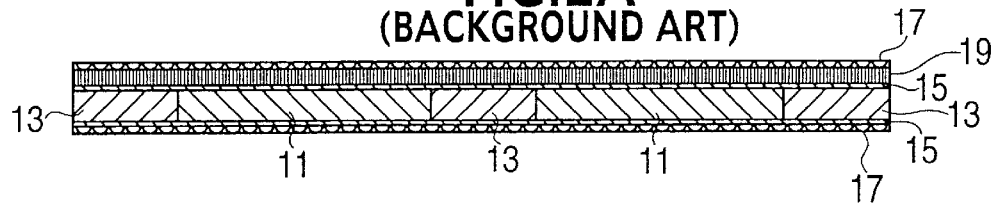
FIGS. 2A and 2B are cross-sectional views of conventional heating/cooling packages incorporating thermoelectric modules.
Figure 2B:
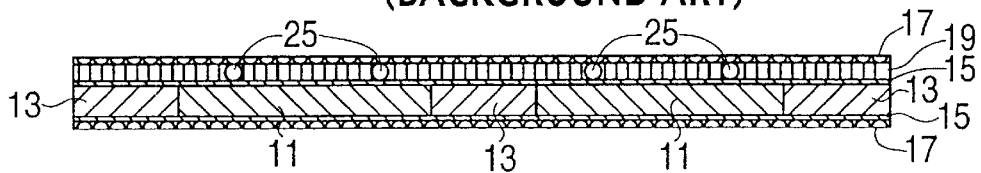

FIG. 2A depicts an implementation of a thermoelectric module in a heating or cooling package. A thermoelectric module or an array of thermoelectric modules 11 is surrounded by a thermal conduction layer of flexible insulating material 13 to prevent heat transfer away from the thermoelectric modules. The hot or cold plates of each thermoelectric module 11 are thermally connected to the respective plates of adjacent thermoelectric modules by flexible conductors 15, for example thin flexible copper with a thermally conductive adhesive backing. The entire package is covered with a flexible thermally conductive material 17, for example a thermally conductive breathable fabric. The item being cooled, for example skin, is placed on the inner side, and the heat is transferred to the surrounding medium on the outer side, for example air. On the outer side of the unit, an additional layer 19 may be used to facilitate heat transfer from the inner or cold layer to outer or hot layer and to provide a protective barrier from the hot thermoelectric module plate. This might be a flexible thermally conductive honeycomb material which acts as a number of individual heat fins in a thermally connected array. Alternatively, this might be a liquid layer, for example water, which acts to convect the heat away from the hot side of the thermoelectric module to the surrounding environment using either natural of forced convection By way of example, an included fluid transfer device, for example a pump, might be used, together with individual heat transfer devices such as single or multi-pass tubes 25 containing all appropriate heat transfer medium, for example water, as shown in FIG. 2B, to remove the heat from the hot side of the thermoelectric module array, the tubes 25 being connected in either a series or parallel fashion to transfer the heat to another location where an alternate device can remove the heat.

FIG. 3A is a schematic representation of a thermoelectric module 10a in accordance with an embodiment of the present invention. Module 10a includes a first thermal conduction layer or substrate panel 12 and a second thermal conduction layer or substrate panel 14, as well as a number of semiconductor pellets and electrically conductive strips (not shown). A thermal barrier 16 surrounds the semiconductor pellets and conductive strips, inhibiting heat transfer between the substrate panels 12 and 14. Preferably, thermal barrier 16 is formed by enclosing the complete thermoelectric module 10a and then evacuating the resulting interior area. The vacuum inhibits heat transfer by convection and conduction between substrate panels 12 and 14 Alternatively thermal barrier 16 might be formed by filling the area around the semiconductor pellets and conductive strips between substrate panels 12 and 14 with an electrically nonconductive thermal insulating material to inhibit heat transfer by convection and radiation between the substrate panels.

First substrate panel 12 includes an address contact area 18. An electrical conductor 20 contacts area 18. Second substrate panel 14 likewise has an address contact area (not shown). Second substrate panel 14 is positioned on a ground plane 22. Ground plane 22 might extend a considerable distance either in one dimension as illustrated in FIG. 2, or in two dimensions, permitting positioning of multiple thermoelectric modules on the same ground plane. When a voltage is applied across conductor 20 and ground plane 22, the current through the semiconductor pellets results in a temperature difference between substrate panels 12 and 14. Thus, for example, a voltage of a first polarity across conductor 20 and ground plane 22 will result in a current in a first direction, causing an increase in the temperature of first substrate panel 12 and a decrease in temperature of second substrate panel 14. If the voltage polarity is reversed, then the current direction reverses, and so the temperature of first substrate panel 12 decreases, while the temperature of second substrate panel 14 increases.

FIG. 3B depicts another embodiment of a thermoelectric module 10b in which address contact area 18 of first substrate panel 12 contacts a first electrical conductor 20, while the address contact area of second substrate panel 14 contacts a second electrical conductor 20'. The provision of electrical conductors in contact with each substrate panel 12, 14 permits selection and/or reversal of the polarity of the voltage applied across module 10b, and so control of which of the substrate panels 12, 14 is heated and which is cooled.

FIG. 3C depicts a further embodiment of a thermoelectric module 10c in which conductors 20a and 20b both contact first substrate panel 12 through corresponding contact areas 18 and 18', while a contact area of second substrate panel 14 is positioned on ground plane 22. Conductor 20a might be coupled to a positive voltage source, while conductor 20b is coupled to a negative voltage source, thereby permitting selection and/or reversal of the polarity of the voltage applied across module 10c, and so control of which of the substrate panels 12, 14 is heated and which is cooled.

Figure 4A:
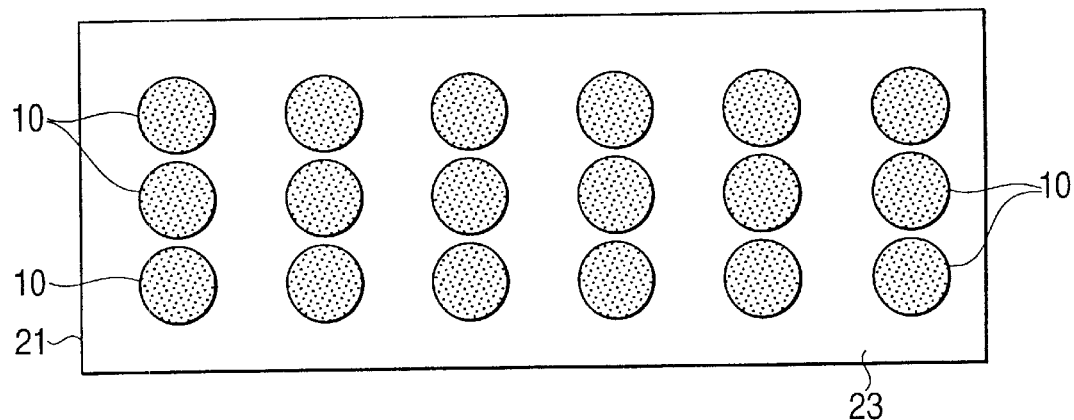

A number of thermoelectric modules 10 (i.e. 10a, 10b, or 10c, or a combination of these) can be provided on a single support member to form a heating and cooling apparatus in accordance with the present invention. The modules can be arranged in a random manner or in a preselected pattern. Thus, FIG. 4A illustrates a heating and cooling apparatus 21 including a number of thermoelectric modules 10 in an isotropic pattern on support surface 23. In FIG. 4A, each thermoelectric module 10 is positioned with the corresponding one of its thermal conduction layers 12, 14 adjacent support surface 23. As a consequence, if each thermoelectric module is provided with voltage of the same polarity, the first substrate panel 12 of each thermoelectric module experiences substantially the same temperature change, for example increasing in temperature, while the second substrate panel 14 of each module experiences the same temperature change, for example decreasing in temperature. Support surface 23 might be formed into or incorporated in a heating and cooling apparatus of any suitable type. By way of example support surface 23 might be incorporated in a portable cooler such as a picnic cooler or such as a cooler for holding critical material, for example blood during transport. When the heating and cooling apparatus is incorporated into a picnic cooler or similar object, power can be provided to the thermoelectric modules by a solar cell.

Likewise, support surface 23 might be incorporated into an item of wearing apparel, for example, a thermally controlled suit to protect a fireman who is entering a burning building from being injured by dangerously high temperatures. Further, the support surface might be incorporated into a blanket, for example to maintain the temperature of a burn victim at a desired level. Similarly, the support surface might be incorporated into a wrap adapted to be positioned around an injured part of a person's body to heat or cool the injured part.

Figure 4B:
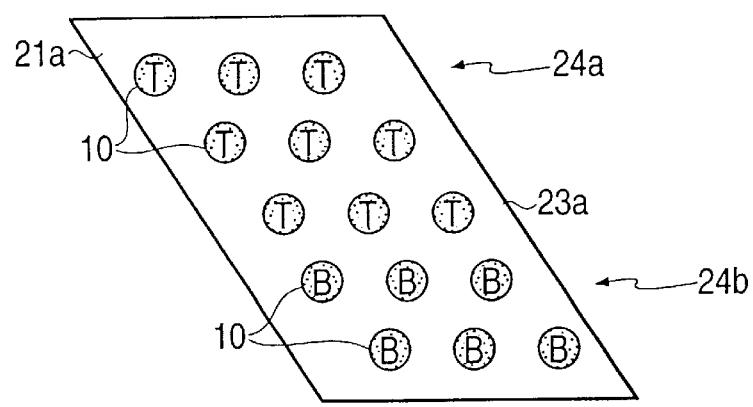

FIG. 4B illustrates an embodiment of a heating and cooling apparatus 21a in which a first group 24a of thermoelectric modules 10 is mounted on support surface 23a with their first substrate panels or tops exposed and their second substrate panels or bottoms adjacent the support surface, while a second group 24b of thermoelectric modules is mounted on the support surface 23a with their first substrate panels 12 or tops adjacent the support surface 23a and their second substrate panels or bottoms exposed. When a uniform voltage is applied to the thermoelectric modules to decrease the temperature of the second substrate panels 12 of group 24a and to increase the temperatures of the first substrate panels 14 of group 24b, a portion of an object contacting the portion of support surface 23a adjacent group 24a is cooled, while another portion of the object contacting, the portion of support surface 23b adjacent group 24b is heated. Reversal of the voltage direction reverses the heating or cooling of the respective groups of modules.

Figure 4C:
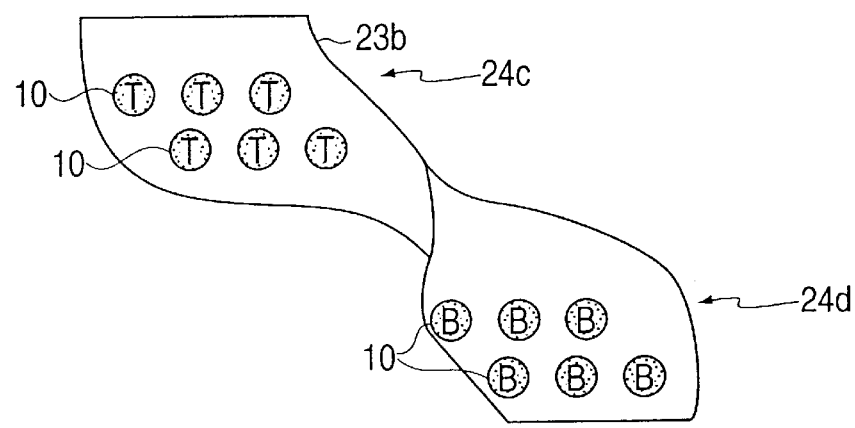

FIG. 4C illustrates a variation in which all of the thermoelectric modules 10 are mounted on a support surface 23b with their first thermal conductive layers or tops exposed and their second thermal conductive layers or bottoms 14 adjacent the support surface. The support surface is provided with a half twist, turning it to 180°, so as to provide a first portion 24c in which the temperature of an object contacting support surface 23b changes in one direction and a second portion 24d in which the temperature of an object contacting the support surface 23b changes in the other direction.

Figure 4D:
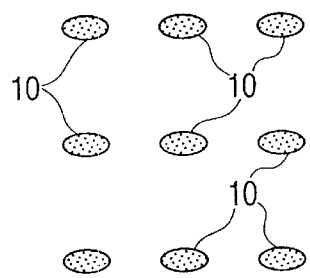
Figure 4E:
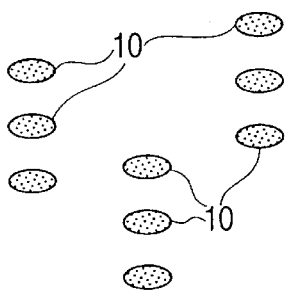
Figure 4F:
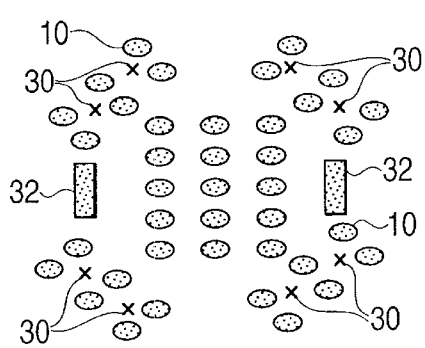
Figure 4G:
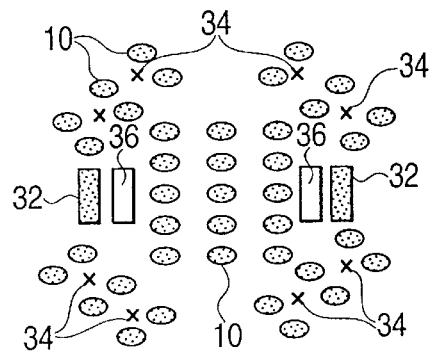

FIG. 4D illustrates a number of thermoelectric modules 10 in a symmetrical anisotropic pattern on a support surface (not shown). FIG. 4E illustrates a number of thermoelectric modules in an asymmetrical anisotropic pattern. FIG. 4F depicts a number of thermoelectric modules 10 in a pattern with temperatures sensors 30 interspersed among the thermoelectric modules to sense the temperatures of the modules. FIG. 4F additionally depicts pressure devices 32 incorporated in the heating and cooling apparatus to apply pressure to a body to which the heating and cooling apparatus is applied. FIG. 4G depicts a number of thermoelectric modules 10 with a number of electrical contacts 34 interspersed among the modules to apply an electrical stimulus to an object to which the heating and cooling apparatus is applied, as well as pressure devices 32. By way of example, the pressure devices 32 might be provided with a liquid or with compressed air from a portable source incorporated in the heating and cooling apparatus, or by material that expands or contracts upon heating) or cooling. If desired, pressure sensors 36 can be included to sense the pressure applied by pressure devices 32.

FIG. 5 is a block diagram of an embodiment of a heating and cooling apparatus in accordance with the present invention. A voltage source 40 includes a controller 42 for controlling voltage to be applied to an array 44 of thermoelectric modules. Voltage source 40 further includes a controller battery 46 for providing power to controller 42. Controller 42 might include a read only memory or a field programmable gate array, by way of examples. In one embodiment, controller 42 includes a processor and a memory which stores a program for the processor In such event, voltage source 40 may include an input unit 48 for receiving input signals from a signal source 50. Input unit 48 might be a jack adapted for connection to signal source 50 by a cable, or might be a wireless receiver for receipt of signals from a wireless signal source over a short range wireless communication and control link such as a Bluetooth connection. Alternatively, signal source 48 might be a keypad on the heating and cooling apparatus signal source 48 call provide different programs to the memory of controller 42 to control thermoelectric module array 44 under different conditions. For example, if controller 42 is a processor and a memory, signal source 48 can provide programs for storage in the memory to control application of voltage to array 44. Controller 42 can also include an authorization unit to receive all authorization code or password to authenticate that the received program is from an authorized source or an authorized individual.

Controller 42 is coupled through address register 52 to thermoelectric module array 44. Appliance battery 54 is also coupled through address register 52 to array 44 to provide positive and negative voltage levels. Address register 52 contains addresses for the thermoelectric modules in array 44. As one example, address register 52 might comprise a bit nap.

In its simplest form, controller 42 can simply be a power supply and an on-off control. In such an apparatus, the voltage source would provide a uniform voltage to each thermoelectric module in array 44 of the heating and cooling apparatus. Alternatively, controller 42 can include an adjustable control to vary the voltage level in a controlled manner.

In one embodiment, controller 42 can cause different thermoelectric modules in array 44 to receive different voltage signals so as to provide different pre-selected temperatures from each thermoelectric module.

Controller 42 applies voltage control and address control signals to address register 50 indicating addresses of thermoelectric modules in array 44 and the voltage signals to be applied to the modules at those addresses. Address register 50 enables those modules to receive the appropriate voltage from appliance battery 54. If array 44 includes temperature sensors 30 or pressure sensors 36, then controller 42 receives temperature signals or pressure signals through address register 50 which indicate the temperature or pressure at each sensor. Controller 42 might control the voltages to limit the rate of change of the temperature of the modules, limit the maximum temperature of the modules, limit the minimum temperature of the modules, or any combination of these, based on the sensed temperatures. Additionally, controller 42 can control the electrical stimulus offered by contacts 34 and the pressure applied by pressure devices 32.

Voltage source 40 might be capable of providing an adjustable level of power to the thermoelectric modules within array 44. FIG. 6A is a timing diagram illustrating, first, a low power condition ill which a comparatively low voltage level is applied to the thermoelectric modules, and, second, a high power condition in which a higher voltage level is applied to the thermoelectric modules. Controller 42 might permit different voltage levels to be applied to different ones of the thermoelectric modules in array 46 if desired, permitting a varying temperature over the surface of the heating and cooling apparatus.

FIG. 6B is a timing diagram illustrating an alternative way of providing low or high power to the thermoelectric modules. Voltage source 40 provides pulses of voltage of uniform level, and controller 42 controls the pulse durations. FIG. 6B illustrates a low power condition in which short pulses are provided, and alternatively, a high power condition in which pulses of a longer duration are provided. Controller 42 might permit pulses of different durations to be applied to different ones of the thermoelectric modules within array 44, if desired, permitting a varying temperature over the surface of the heating and cooling apparatus.

FIG. 6C is a timing diagram illustrating the application of voltage which periodically varies in direction or polarity to a heating and cooling apparatus in accordance with the present invention. Although a substantially sinusoidal waveform is shown, other waveforms could be utilized. As the voltage reverses polarity, the substrate panel 12 or 14 which is heated reverses, as does the substrate panel 14 or 12 which is cooled. The duration of the heating/cooling cycle can be controlled to fit a particular need, and, for example, might be anywhere from several microseconds to an hour or longer.

FIG. 7 depicts a thermoelectric module array control technique using gate devices G1, G2, G3 and G4 in a bridge arrangement to control the state of the thermoelectric modules—i.e. heating, cooling, or inactive. The four gate devices, G1, G2, G3 and G4 are connected in a bridge architecture through resistor R to battery B, with the thermoelectric module in the common branch of the bridge. Two digital control signals control the circuit operation.

When "control signal 1 is high, and "control signal 2 is low, gates G1 and G4, conduct, and gates G2 and G3 are blocked. The positive voltage from battery B is connected to the thermoelectric module at terminal A, while the thermoelectric module is connected to battery ground via terminal B. When "control signal 2 is high, and "control signal 1 is lows, gates G1 and G4 are blocked and gates G2 and G3 are on. The positive battery voltage is connected to the thermoelectric module at terminal B, and the thermoelectric module is connected to battery ground via terminal A. Current flows in the opposite direction, and the thermoelectric module state is reversed. When both signals are low, the thermoelectric module is inoperative. Both signals high is a prohibited state, but does not damage the thermoelectric module. Resistor limits the level of the current into the thermoelectric module, and so limits the rate of heating. CMOS inverters call be used to implement the architecture.

Figure 8A:
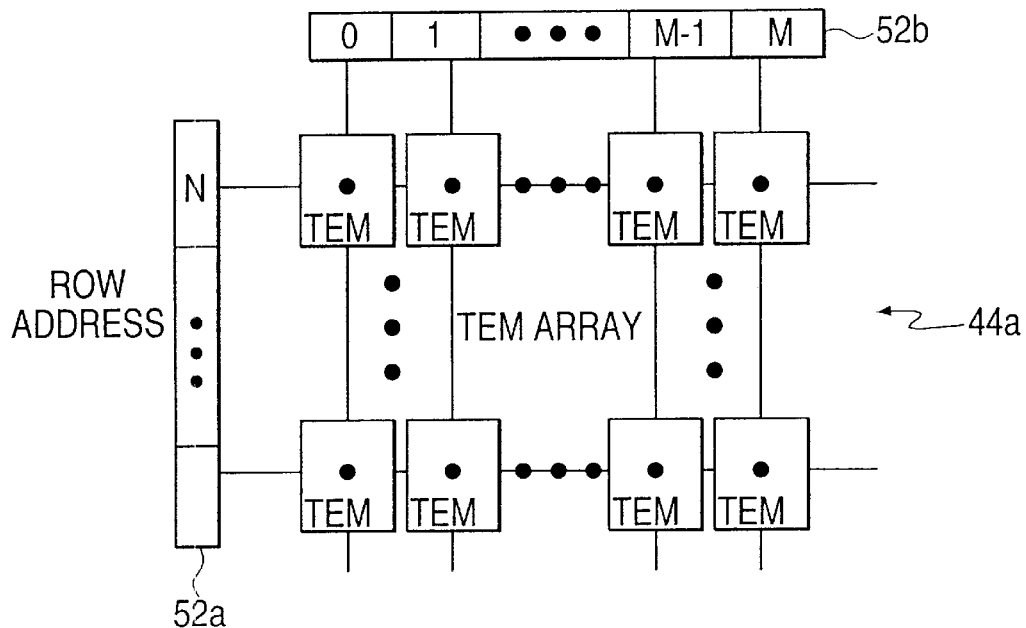
Figure 8B:
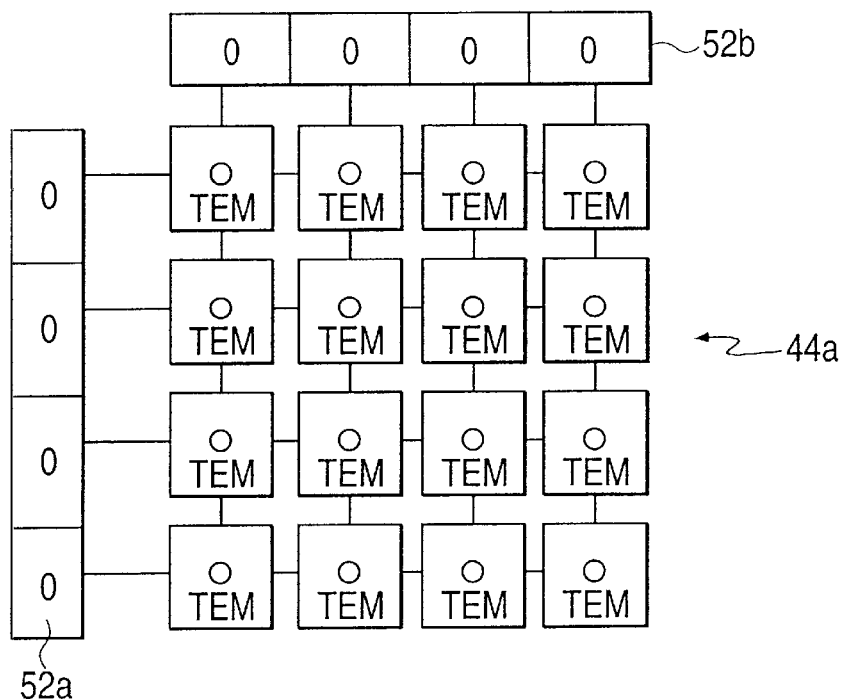
Figure 8C:
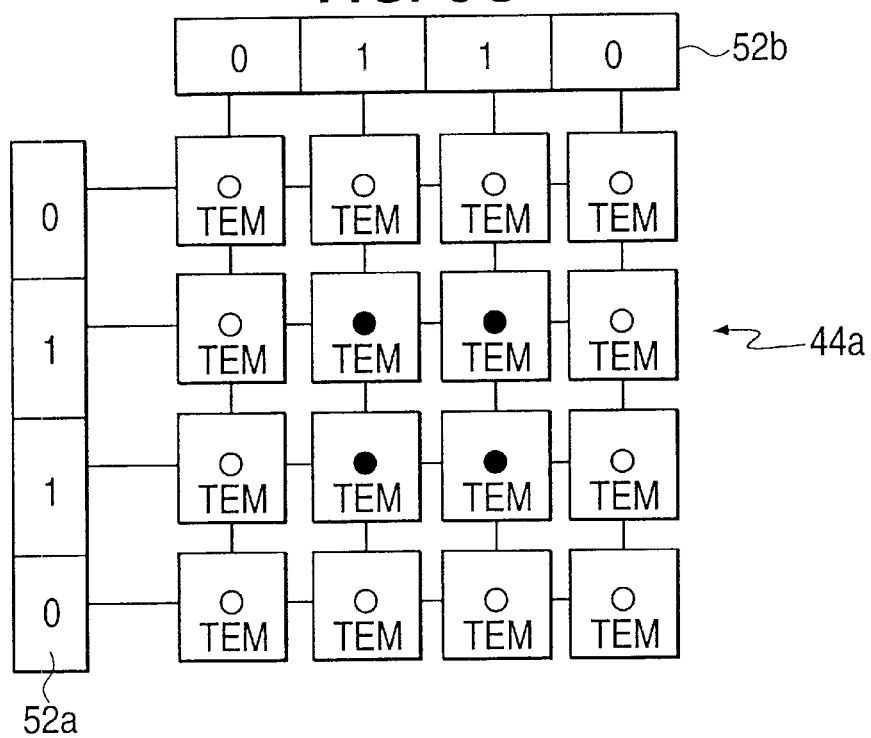
Figure 8D:
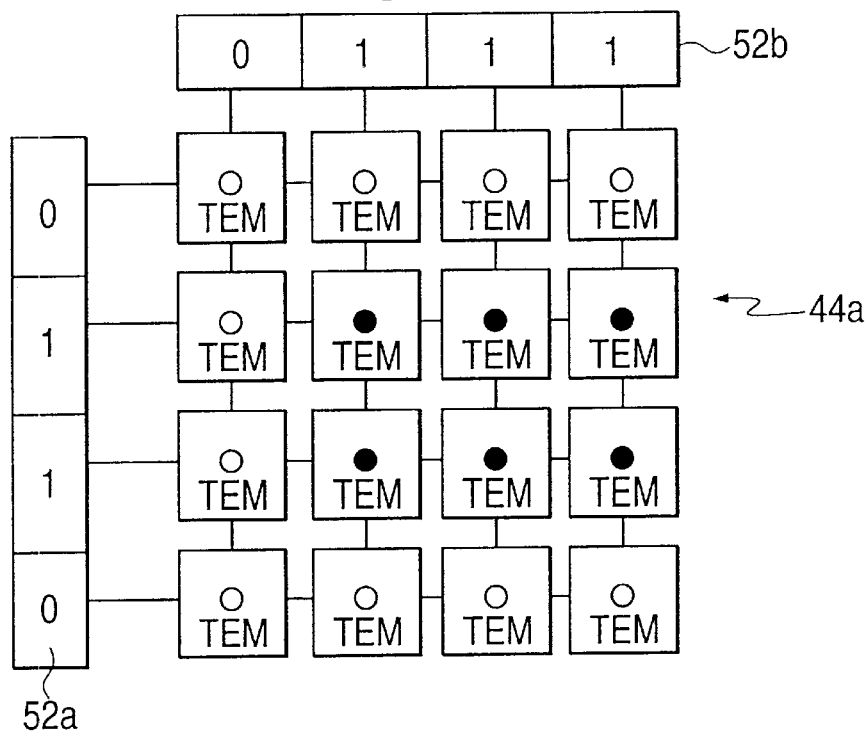

FIG. 8A illustrates a thermoelectric module array 44a in the form of a plurality of rows and a plurality of columns. An addressing unit for the array includes a row address section 52a and a column address section 52b. Row address section 52a includes a cell for each row of array 44a, and column address section 52b includes a cell for each column of array 44a. When one or more of the cells of row address section 52a and one or more of the cells of column address section 52b are energized, each thermoelectric module at an intersection of an energized row address cell and an energized column address cell receives power, resulting in a temperature change. FIG. 8B illustrates a state in which no cell is energized, as indicated by the binary zeros in all the cells in row address section 52a and in column address section 52b. In this state no thermoelectric module is energized FIG. 8C illustrates the center two row address cells energized and the center two column address cells energized, as indicated by the binary ones in those cells. As a result, the four center-most thermoelectric modules are energized, as indicated by the black dots in their centers. FIG. 8D illustrates the center two row address cells and the right-most three column address cells energized, resulting in energization of the six thermoelectric modules depicted with black centers.

FIG. 9 illustrates all addressing scheme in which each thermoelectric module is assigned an address, and address register 52c includes a cell corresponding to each module. Each cell then either applies voltage to its corresponding thermoelectric module or blocks voltage to the module, as directed by controller 42, resulting in either a temperature change at the module or not.

Figure 10B:
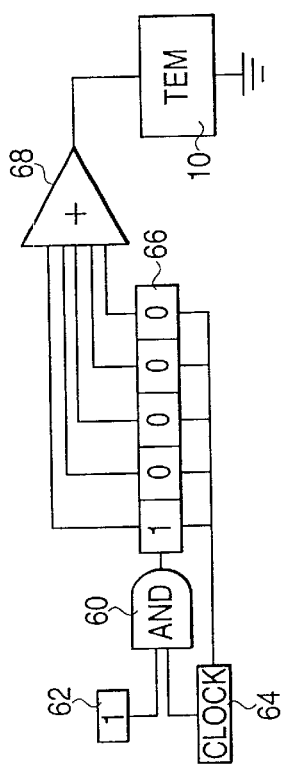
Figure 10D:
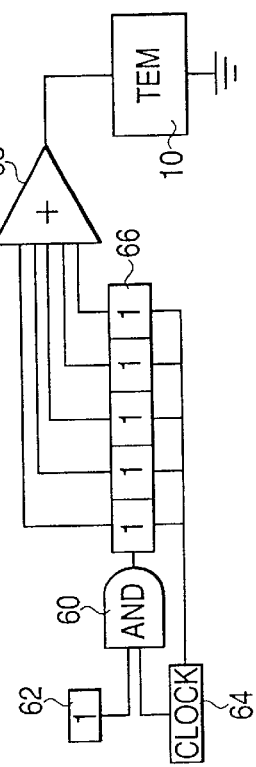
Figure 10A:
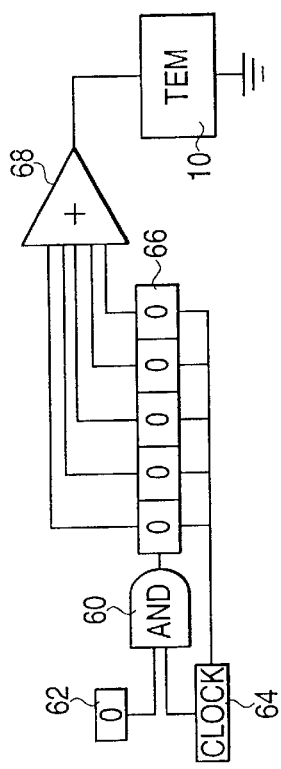
Figure 10C:
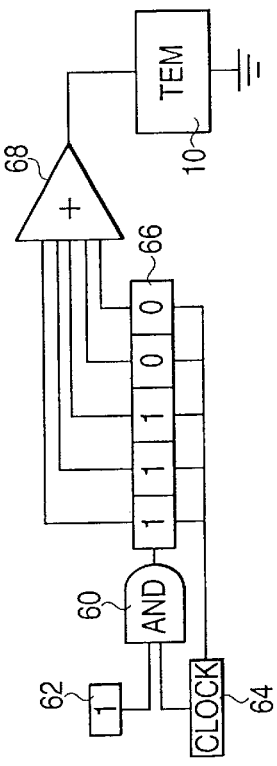

FIGS. 10A–10D illustrate an addressing scheme in which an AND gate 60 has its first input connected to a signal source 62 and its second input connected to a clock 64. The output of AND gate 60 is connected to the signal input of a shift register 66, depicted in the illustrative showing of FIGS. 10A–10D as having five stages. Each stage of the shift register has its control input connected to clock 64 and its output connected to an input of a summing circuit 68, the output of which is connected to thermoelectric module 10. Preferably, this connection is through an address register such as address register 52, accommodating an array of thermoelectric modules. FIG. 10A illustrates a condition in which each stage of shift register 66 stores a binary zero so that the output of summing circuit 68 is a zero value. As a result thermoelectric module 10 does not change in temperature. FIG. 10B illustrates a condition in which signal source 62 has applied a binary one. As a result, at the next pulse from clock 64 the first stage of shift register 66 stores a binary one and applies a signal to summing circuit 68, resulting in a low level of voltage to module 10, causing a low temperature change. FIG. 10C illustrates a condition in which three stages of shift register 66 store binary ones, applying three signals to summing circuit 68, which therefore applies a moderate voltage level to thermoelectric module 10, causing a moderate temperature change. FIG. 10D illustrates a maximum temperature change, with all five stages of shift register 66 storing binary ones, and so applying signals to summing circuit 68 so that the summing circuit applies a high voltage level to module 10, causing a high temperature change.

FIG. 11 schematically illustrates a heating and cooling apparatus in accordance with a further embodiment of the present invention. A first thermoelectric module 70 is connected across a voltage source 72 FIG. 11 illustrates the upper thermal conduction layer 12 as increasing in temperature, while the lower thermal conduction layer 14 decreases in temperature. A thermal conductor 74 couples a thermal contact 76 on layer 12 of thermoelectric module 70 to a thermal contact 76a on the thermal conduction layer 12a of a second thermoelectric module 70a. The lower thermal conduction layer 14a of thermoelectric module 70a is connected to a heat sink (not shown) or is at ambient temperature.

Voltage source 72 results in a voltage difference across the two thermal conduction layers 12 and 14 of thermoelectric module 70, resulting in the upper thermal conduction layer 12 of module 70 increasing in temperature. Thermal conductor 76 conducts heat from the upper thermal conduction layer of thermoelectric module 70 to the upper thermal conduction layer 12a of thermoelectric module 70a, resulting in a temperature difference across the two thermal conduction layers 12a and 14a of module 70a. As a consequence, a voltage difference is generated between layers 12a and 14a of module 70a. An electrical utilizing device 78 is connected across layers 12a and 14a to utilize this voltage difference. By way of example, device 78 might be a volt age sensor which detects the voltage difference. The detected voltage difference then might be used as an indication of the temperature difference between the two thermal conduction layers 12 and 14 of module 70, and thus an indication of the temperature of an object contacting thermal conduction layer 12.

The present invention thus provides improved thermoelectric modules and improved heating and cooling apparatuses incorporating thermoelectric modules. Although the invention has been described with reference to preferred embodiments, various modifications, alterations, rearrangements and substitutions might be made, and still the result would come within the scope of the invention.

What is claimed is:

1. A heating and cooling apparatus adapted to be applied to an object to control the temperature of the object, said heating and cooling apparatus comprising:
   a plurality of thermoelectric modules arranged in a substantially planar two-dimensional pattern and adapted to contact the object; and
   a power source coupled to said thermoelectric modules to cause a temperature change in each thermoelectric module so as to control the temperature of the object in accordance with the pattern.

2. A heating and cooling apparatus as claimed in claim 1, wherein said thermoelectric modules are arranged in an isotropic pattern.

3. A heating and cooling apparatus as claimed in claim 1, wherein said thermoelectric modules are arranged in an anisotropic pattern.

4. A heating and cooling apparatus as claimed in claim 3, wherein said pattern is symmetrical.

5. A heating and cooling apparatus as claimed in claim 3, wherein said pattern is asymmetrical.

6. A heating and cooling apparatus as claimed in claim 1, wherein each of said thermoelectric modules has a first surface and a second surface, and each module is responsive to applied voltage of a given polarity to increase the temperature of its first surface and to decrease the temperature of its second surface, and wherein the first surfaces of said thermoelectric modules define a substantially continuous surface.

7. A heating and cooling apparatus as claimed in claim 1, wherein each of said thermoelectric modules has a first surface and a second surface, and each module is responsive to applied voltage of a given polarity to increase the temperature of its first surface and to decrease the temperature of its second surface, and wherein said apparatus has a substantially continuous surface including a first portion defined by the first surfaces of some of said thermoelectric modules and a second portion defined by the second surfaces of others of said thermoelectric modules.

8. A heating and cooling apparatus as claimed in claim 7, wherein said substantially continuous surface further includes a twisted portion joining said first portion and said second portion.

9. A heating and cooling apparatus as claimed in claim 1, further comprising an electrical stimulating device to apply an electrical stimulus to the object.

10. A heating and cooling apparatus as claimed in claim 1, further comprising a pressure device to apply pressure to the object.

11. A heating and cooling apparatus as claimed in claim 10, further comprising a pressure sensor for sensing the pressure applied to the object, and a controller responsive to the sensed pressure for controlling the pressure device to control the applied pressure.

12. A heating and cooling apparatus as claimed in claim 1, further comprising a temperature sensor for sensing the temperature of said thermoelectric modules and a controller responsive to the sensed temperature for controlling said power source to control the temperature change.

13. A heating and cooling apparatus as claimed in claim 12, wherein said controller is adapted to control the rate of change of temperature of said thermoelectric module.

14. A heating and cooling apparatus as claimed in claim 12, wherein said controller is adapted to control the maximum temperature of said thermoelectric modules.

15. A heating and cooling apparatus as claimed in claim 12, wherein said controller is adapted to control the minimum temperature of said thermoelectric modules.

16. A heating and cooling apparatus as claimed in claim 1, wherein said power source applies a constant voltage to said thermoelectric modules.

17. A heating and cooling apparatus as claimed in claim 1, wherein said power source comprises a voltage supply for supplying a voltage to said thermoelectric modules, and a controller for controlling the supplied voltage.

18. A heating and cooling apparatus as claimed in claim 17, wherein said voltage source further comprises an input unit connected to said controller for receiving input signals and applying the received input signals to said controller to determine the control of the supplied voltage.

19. A heating and cooling apparatus as claimed in claim 18, wherein said input unit comprises a wireless receiver for receiving the input signals from a wireless source.

20. A heating and cooling apparatus as claimed in claim 19, wherein said wireless receiver comprises a short range wireless communication and control link.

21. A heating and cooling apparatus as claimed in claim 20, wherein said wireless receiver comprises a Bluetooth receiver.

22. A heating and cooling apparatus as claimed in claim 18, wherein said controller further comprises an authentication unit for receiving an authentication code authenticating the received input signals as being from an authorized source.

23. A heating and cooling apparatus as claimed in claim 17, wherein said controller comprises a read only memory.

24. A heating and cooling apparatus as claimed in claim 17, wherein said controller comprises a processor for controlling the supplied voltage, and a memory for storing a program for said processor.

25. A heating and cooling apparatus as claimed in claim 24, wherein said controller further comprises an input unit for receiving a program for storage in said memory, permitting changing of the stored program.

26. A heating and cooling apparatus as claimed in claim 25, wherein said input unit comprises a wireless receiver for receiving the program from a wireless source.

27. A heating and cooling apparatus as claimed in claim 26, wherein said wireless receiver comprises a short range wireless communication and control link.

28. A heating and cooling apparatus as claimed in claim 27, wherein said wireless receiver comprises a Bluetooth receiver.

29. A heating and cooling apparatus as claimed in claim 25, wherein said controller further comprises an authentication unit for receiving an authentication code authenticating the received program as being from an authorized source.

30. A heating and cooling apparatus as claimed in claim 17, wherein said controller is adapted to vary the voltage level.

31. A heating and cooling apparatus as claimed in claim 30, wherein said controller comprises a shift register having a plurality of stages, a pulse source for selectively applying signals in sequence to the stages of said shift register, and a summing circuit for summing the signals within the stages of said shift register to provide a voltage level signal to determine the level of the voltage.

32. A heating and cooling apparatus as claimed in claim 30, wherein said controller causes said voltage source to apply voltages of different voltage levels to different ones of said thermoelectric modules.

33. A heating and cooling apparatus as claimed in claim 32, wherein said controller comprises an addressing unit for indicating the different ones of said thermoelectric modules to which the different voltage levels are to be applied.

34. A heating and cooling apparatus as claimed in claim 33, wherein said controller includes a memory map of said thermoelectric modules, and said addressing unit selects locations on said memory map to indicate the different ones of said thermoelectric modules.

35. A heating and cooling apparatus as claimed in claim 17, wherein said controller causes said voltage source to apply pulses of voltage to said thermoelectric modules, and said controller varies the durations of the voltage pulses.

36. A heating and cooling apparatus as claimed in claim 35, wherein said controller controls said power supply to apply voltage pulses of different durations to different ones of said thermoelectric modules.

37. A heating and cooling apparatus as claimed in claim 36, wherein said controller comprises an addressing unit for indicating the different ones of said thermoelectric modules to which pulses of different durations are to be applied.

38. A heating and cooling apparatus as claimed in claim 37, wherein said controller includes a memory map of said thermoelectric modules, and said addressing unit selects locations on said memory map to indicate the different ones of said thermoelectric modules.

39. A heating and cooling apparatus as claimed in claim 17, wherein said controller is adapted to vary the voltage polarity.

40. A heating and cooling apparatus as claimed in claim 17, wherein said controller comprises a digital controller.

41. A heating and cooling apparatus as claimed in claim 17, wherein said controller includes a temperature sensor for sensing the temperature of said thermoelectric modules, and a control unit for controlling the applied voltage so as to limit the rate of change of the temperature of said thermoelectric modules.

42. A heating and cooling apparatus as claimed in claim 17, wherein said controller includes a temperature sensor for sensing the temperature of said thermoelectric modules, and a control unit for controlling the applied voltage so as to limit the maximum temperature of said thermoelectric modules.

43. A heating and cooling apparatus as claimed in claim 17, wherein said controller includes a temperature sensor for sensing the temperature of said thermoelectric modules, and a control unit for controlling the applied voltage so as to limit the minimum temperature of said thermoelectric modules.

44. A heating and cooling apparatus as claimed in claim 1, wherein said thermoelectric modules are arranged in an array of a plurality of rows and a plurality of columns, each column intersecting each of said plurality of rows.

45. A heating and cooling apparatus as claimed in claim 1, wherein said voltage source comprises a solar cell.

46. A heating and cooling apparatus as claimed in claim 1, further comprising a cooler housing having said thermoelectric modules incorporated therein to provide a cooler for cooling items.

47. A heating and cooling apparatus as claimed in claim 1, further comprising an item of wearing apparel having said thermoelectric modules incorporated therein to maintain the temperature of a wearer at a temperature different from surrounding ambient temperature.

48. A heating and cooling apparatus as claimed in claim 1, further comprising a blanket having said thermoelectric modules incorporated therein to maintain the temperature of an object at a different level from surrounding ambient temperature.

49. A heating and cooling apparatus as claimed in claim 1, further comprising a wrap adapted to be positioned around a part of a human body and having said thermoelectric modules incorporated therein to maintain the body part at a temperature different from surrounding ambient temperature.

50. A heating and cooling apparatus, comprising:
 a first thermoelectric module, including a first thermal conduction panel and a second thermal conduction panel;
 a second thermoelectric module, including a third thermal conduction panel and a fourth thermal conduction panel;
  a power source connected across said first and second thermal conduction panels to provide a voltage difference thereacross so as to raise the temperature of said first thermal conduction panel;
 a thermal conductor thermally connecting said first thermal conduction panel and said third thermal conduction panel to conduct heat from said first thermal conduction panel to said third thermal conduction panel so as to create a temperature difference between said third thermal conduction panel and said fourth thermal conduction panel, resulting in a voltage difference across said third and fourth thermal conduction panels; and
 means connected across said third and fourth thermal conduction panels to utilize the voltage thereacross.

51. A heating and cooling apparatus as claimed in claim 17, wherein said controller comprises a field programmable device.

52. A heating and cooling apparatus as claimed in claim 1, wherein said plurality of thermoelectric modules are arranged in a planar two-dimensional pattern that is flexible to conform with three-dimensional objects.

53. A heating and cooling apparatus as claimed in claim 51, wherein said controller comprises a field programmable gate array.

* * * * *